United States Patent
Wilhelmsson

(10) Patent No.: US 7,286,458 B2
(45) Date of Patent: Oct. 23, 2007

(54) QUALITY-TESTING APPARATUS AND METHOD

(75) Inventor: Ulf Wilhelmsson, Malmö (SE)

(73) Assignee: Audiodeu AB, Malmö (SE)

( * ) Notice: Subject to any disclaimer, the term of this patent is extended or adjusted under 35 U.S.C. 154(b) by 504 days.

(21) Appl. No.: 10/825,125

(22) Filed: Apr. 16, 2004

(65) Prior Publication Data
US 2004/0264307 A1 Dec. 30, 2004

(51) Int. Cl.
*G11B 5/09* (2006.01)
(52) U.S. Cl. .................. 369/53.1; 369/47.19; 369/59.21
(58) Field of Classification Search ................ None
See application file for complete search history.

(56) References Cited

U.S. PATENT DOCUMENTS 6,188,657 B1 * 2/2001 Kim et al. ............... 369/53.11
6,388,744 B1 5/2002 Kubota

FOREIGN PATENT DOCUMENTS

JP 63201921 8/1988

* cited by examiner

*Primary Examiner*—Muhammad Edun

(57) ABSTRACT

A quality-testing apparatus is disclosed for an optical disk of the type that stores optically readable information in the form of a spiral or annular pattern defining a plurality of essentially concentric tracks. The apparatus has a laser light source and a drive mechanism which projects a laser beam spot from the laser light source onto a surface of the optical disk and moves the projected laser beam spot radically over a portion of the disc surface across at least some of the tracks. A light detector detects a reflection from the projected laser beam spot during its movement. The light detector produces a time variant measurement signal (HF) being associated with passages of the moving laser beam spot across respective tracks. A processing device measures the signal amplitude of selected parts of the optical disk and provides an output comprising key parameters such as symmetry and relative signal strength for the annular pattern of pits and lands.

17 Claims, 5 Drawing Sheets

QUALITY-TESTING APPARATUS AND METHOD

TECHNICAL FIELD

Generally, the present invention relates to test equipment for optical data carriers, and more specifically to an apparatus and method for measuring amplitude parameters received by reading different tracks, for an optical disk of the type that stores optically readable information in the form of a spiral or annular pattern defining a plurality of essentially concentric tracks.

DESCRIPTION OF THE PRIOR ART

Optical data carriers are used for storing very large amounts of digital information, which represent for instance music, images or digital data for computers, such as program files and data files. The most common type of optical data carriers is the compact disk, which is available in several different data formats, among which CD-Audio, CD-ROM, CD-ROM XA, CD-I, CD-R and CD-RW are the most common. The standard for compact disks was established some decades ago and has been in use ever since. In recent years, more sophisticated types of optical data carriers have been introduced; DVD (Digital Versatile Disk) and SACD (Super Audio CD).

A common feature of the compact disks above is that they store very large amounts of information on a small surface. The digital information is read at high precision by means of a laser beam, and even if the information is stored on the compact disks according to error-correcting encoding methods, there is a large demand among manufacturers and distributors of compact disks to be able to quality check the production of the compact disks. It is an absolute requirement to fulfill the specifications from Philips and Sony for CD, and from The DVD Group for DVD, so as to ascertain a minimal number of errors and deficiencies among the compact disks, mainly in their information-carrying layer.

When checking the quality of compact disks, a variety of parameters are measured and registered, both physical parameters (such as skewness, eccentricity, cross talk, etc.) and logical errors (various rates of bit errors, block errors and burst errors). Other important parameters are the degree of birefringence in the transparent plastic layer of the compact disk and so-called jitter, i.e. statistical time variations in the signal obtained when reading or playing the compact disk. Moreover, a very important parameter related to the quality of the optical disk is the signal amplitude that is obtained when reading the optical disk.

As is generally known, a normal audio CD is based on an about 1.2 mm thick plastic disk having a diameter of 12 cm. The plastic disk is normally manufactured as an injection-molded piece of clear polycarbonate plastic. During manufacturing, the plastic disk is impressed with microscopic bumps arranged as a single, continuous spiral pattern that represents the information stored on the CD. A stamper is used for impressing this spiral pattern of microscopic bumps. Once the clear piece of polycarbonate disk has been formed, a thin reflective aluminum layer is sputtered onto the disk, thereby covering the spiral pattern of bumps. Then, a thin photopolymer layer is applied to the aluminum to protect it. Finally, a CD label is printed onto the photopolymer layer.

The bumps in the spiral pattern are normally referred to as pits, since this is how they appear when viewed from the aluminum layer. The areas between adjacent pits are normally referred to as lands or plane areas.

Each turn or revolution of the continuous spiral pattern essentially forms a circular track, which is concentric with the following turn or revolution of the spiral pattern. Therefore, a CD is often described as having a plurality of circular tracks, even if they in reality are coupled to each other in a single continuous spiral pattern. A CD has about 22,000 tracks, whereas a DVD has about 50,000 tracks.

FIG. 1 illustrates an optical disk 1, such as a CD or DVD, with its single continuous spiral pattern 2 of pits and plane areas. As described, the spiral pattern forms a plurality of essentially concentric circular tracks 3. The optical disk 1 has a center opening 5 for engagement with a drive spindle to rotate the optical disk 1.

FIG. 2 illustrates a few tracks 3 in more detail. The pits (or bumps) are indicated at 6, whereas the intermediate plane areas (or lands) are indicated at 7.

As already mentioned, a stamper is used when producing CDs. A disk master is the geometrical origin of a stamper and may be produced by applying a thin layer of photoresist or another removable material onto a glass disk. A mastering device is continuously moved radially from the center of the glass disk towards its periphery and exposes the photoresist layer in a pattern which corresponds to the desired spiral pattern of pits and plane areas on the end product, i.e. the CD. Obviously, it is very important that the pits are clearly distinguishable from the lands on the optical disk. More specifically, pits with different size need to be properly identified when reading the optical disk.

Since the pits of the stamper are not optimized for reading, the HF-signal produced when reading the stamper is different than the HF-signal from the resulting disk.

When manufacturing an optical disk, each production line has its own characteristics regarding how the pit structure is affected between the stamper and the disc. Therefore, the signal output relationships differ between different production lines. For CDs, there are specifications regarding signal levels. There is no corresponding standard for stampers, since a standard is nearly impossible to establish due to different production line characteristics as described above. Consequently, the signal levels obtained when reading a manufactured disk are difficult to predict by examining only the stamper.

It is therefore highly desired to be able to detect signal levels that are too weak for a correct reading of an optical disk.

Today, the entire disk is read in order to measure the signal levels associated with different pit-lengths. In particular the so-called $I_3$ and $I_{11}$ levels are of interest. In case the $I_3$ and $I_{11}$ levels are too low, decoder problems will arise since it will be difficult to obtain a correct reading of the information stored on the optical disk.

SUMMARY OF THE INVENTION

The present invention seeks to provide a fast and automatized method of measuring signal amplitude parameters associated with different pit sizes for an optical disk.

This object has been achieved by an apparatus and a method according to the enclosed independent patent claims.

According to a preferred embodiment, a quality-testing apparatus is provided for an optical disk of the type that stores optically readable information in the form of a spiral or annular pattern defining a plurality of essentially concentric tracks. The apparatus has a laser light source and a drive mechanism, which projects a laser beam spot from the laser light source onto a surface of the optical disk. Moreover, the drive mechanism causes the projected laser beam spot to move radially over the disk surface across the tracks. A light detector is positioned to detect a reflection or $1^{st}$ order diffraction from the projected laser beam spot during its movement. The light detector produces a time variant measurement signal being associated with passages of the moving laser beam spot across respective tracks. A processing device or controller, such as a microprocessor (CPU) with associated software, determines the amplitude of the measurement signal at every time instant and in response provides an output indicative of key parameters such as symmetry and relative signal strength for the annular pattern of pits and lands.

Other objects, features and advantages of the present invention will appear more clearly from the following detailed disclosure of a preferred embodiment.

BRIEF DESCRIPTION OF THE DRAWINGS

A preferred embodiment of the present invention will now be described with reference to the accompanying drawings, in which.

DETAILED DISCLOSURE

Figure 1:
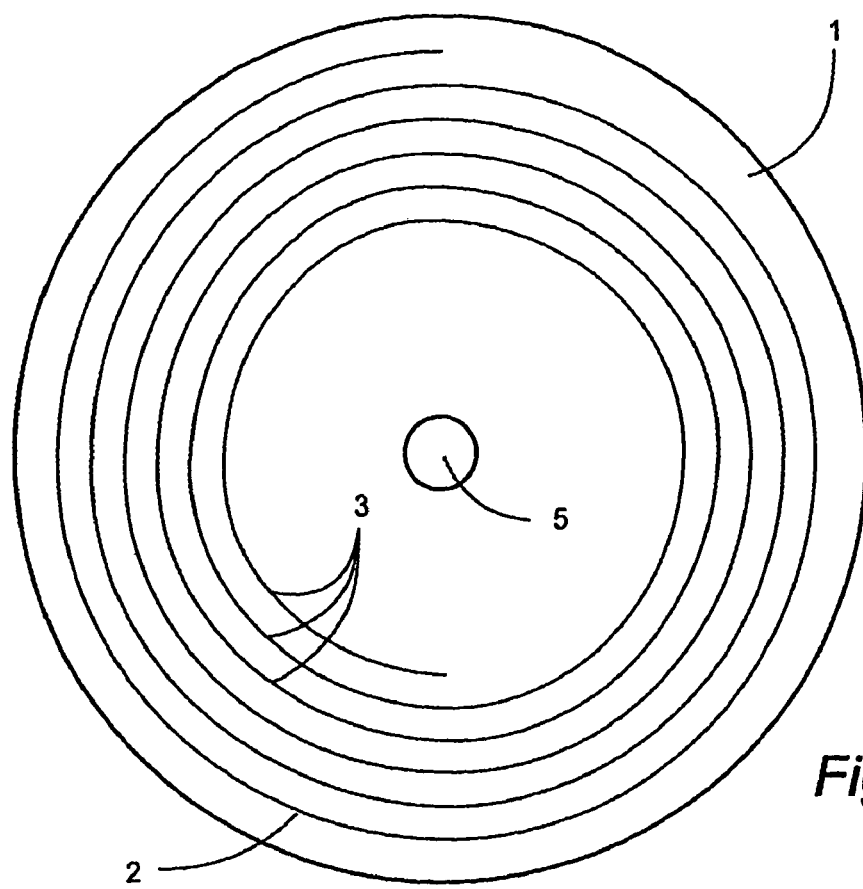
FIG. 1 is a schematic illustration of an optical disk and a continuous spiral pattern forming a plurality of concentric tracks.
Figure 2:
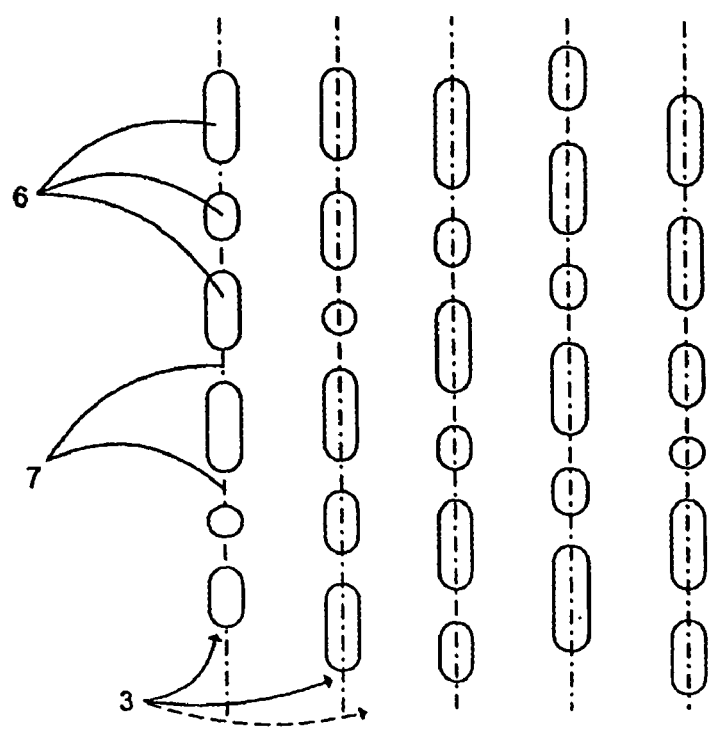
FIG. 2 is a schematic illustration of a small area of a few of the tracks on the optical disk of FIG. 1.
Figure 3:
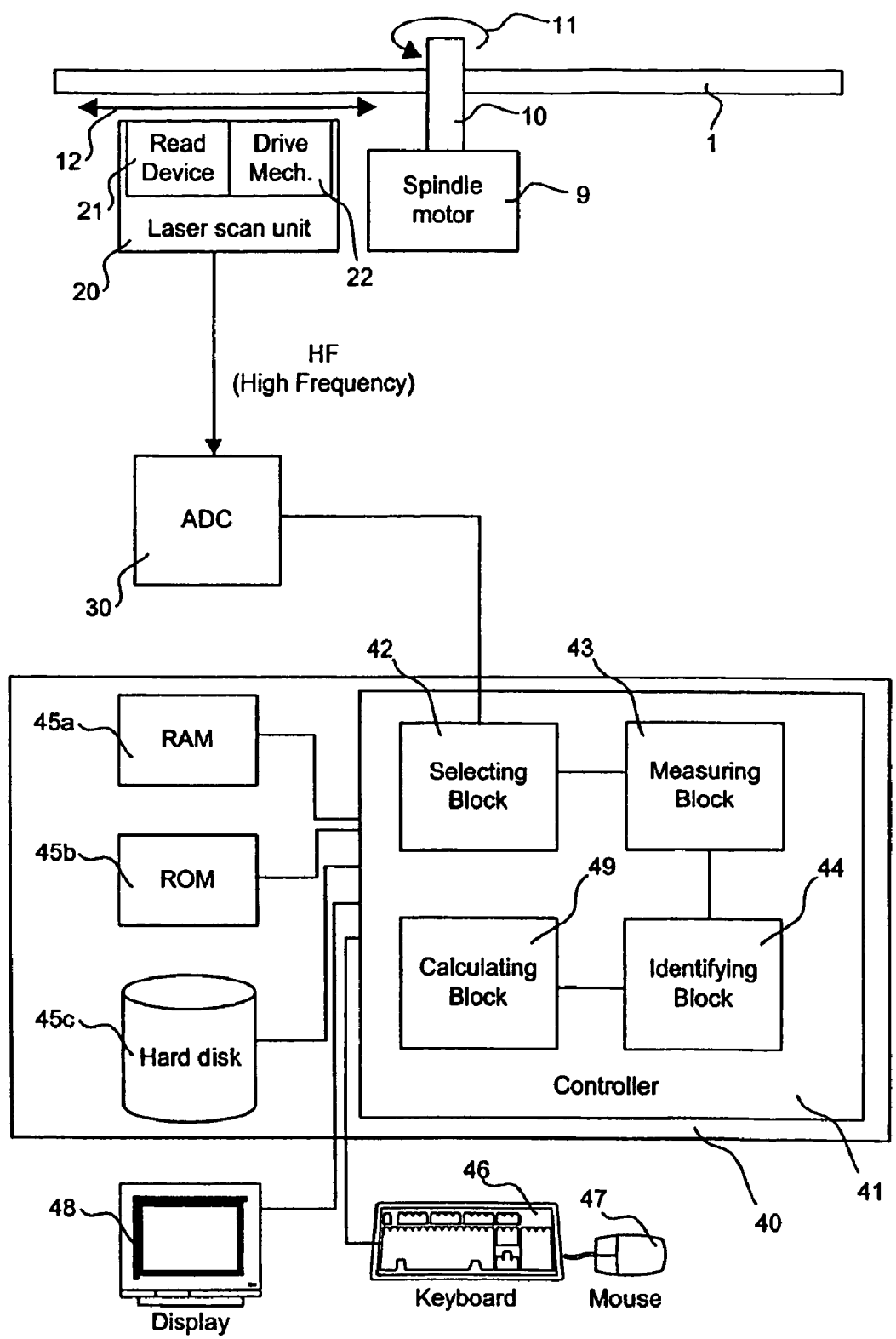
FIG. 3 is a schematic block diagram of a quality-testing apparatus for an optical disk according to the invention.

FIG. 3 gives an overview of a quality-testing apparatus according to a preferred embodiment. A disk drive 9, 10 in the form of a spindle motor 9 and a rotatable spindle 10 is adapted to rotate the optical disk 1 in a direction indicated by 11 in FIG. 3, in a manner which is well known in the art. A laser scan unit 20 is positioned close to one surface of the optical disk 1 and is movable in a radial direction of the optical disk 1, as is indicated by 12 in FIG. 3. The laser scan unit 20 operates to irradiate the surface of the optical disk 1 with a radially sweeping beam of laser light, detect reflections from the surface of the optical disk, produce a time-varying measurement signal in response thereof and provide this signal, labeled HF—High Frequency in the drawings. During the radial scan, the optical disk 1 will be kept in rotation by the disk drive (spindle motor 9 and spindle 10).

As mentioned above, the laser scan unit 20 contains mechanical drive means 22 for causing the optical assembly or optical read device 21 of the laser scan unit 20 to move radially along the surface of the optical disk 1 in the direction 12 indicated in FIG. 3. However, such mechanical drive means 22 are well known per se in the technical field, and it is left to the skilled person to choose the suitable mechanical and electrical components (such as an electric motor and a mechanical carriage arrangement), depending on an actual application. In essence, any equipment will do, which is capable of causing the optical components 21 of the laser scan unit 20 to move with high precision in the desired radial direction. Furthermore, the laser source may be chosen among a variety of commercially available components and may operate in a desired wavelength range, for instance at about 800 nm.

Figure 4A:
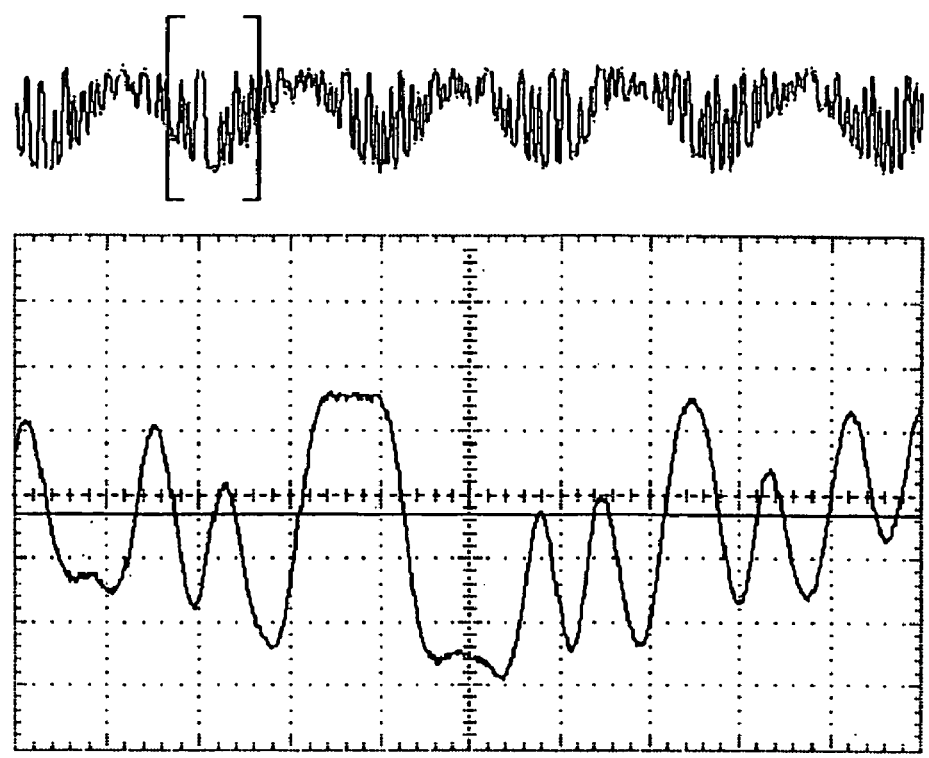
FIG. 4 illustrates the appearance of the measured signal during different instances in the processing chain.

The time-variant output signal HF from the laser scan unit 20 comprises two main signal components as is seen in FIG. 4a. A first, low frequency, envelope signal arises from the intensity variations of the reflected beam from a spot cast by the laser scan unit 20 when it moves in a radial direction over the surface crossing the tracks of the optical disk 1. When the spot is at the center of a pit 6, the intensity of the reflected beam will be minimal and when the spot is at the center of the intermediate flat area between adjacent pits 6 or tracks 3, the intensity of the reflected beam will be maximal.

A second, high frequency, information signal arises from the absorption and reflection of the actual pit 6 and land 7 regions that are present in a track 3.

As can be seen from FIG. 4a, the high frequency information signal is AM-modulated by the low frequency envelope signal. The modulation is special in the sense that the high frequency information signal is not symmetrically modulated by the low frequency signal but rather has a almost fixed upper limit 401 for the amplitude and a lower amplitude limit 402 that is modulated by the envelope signal.

Figure 5:
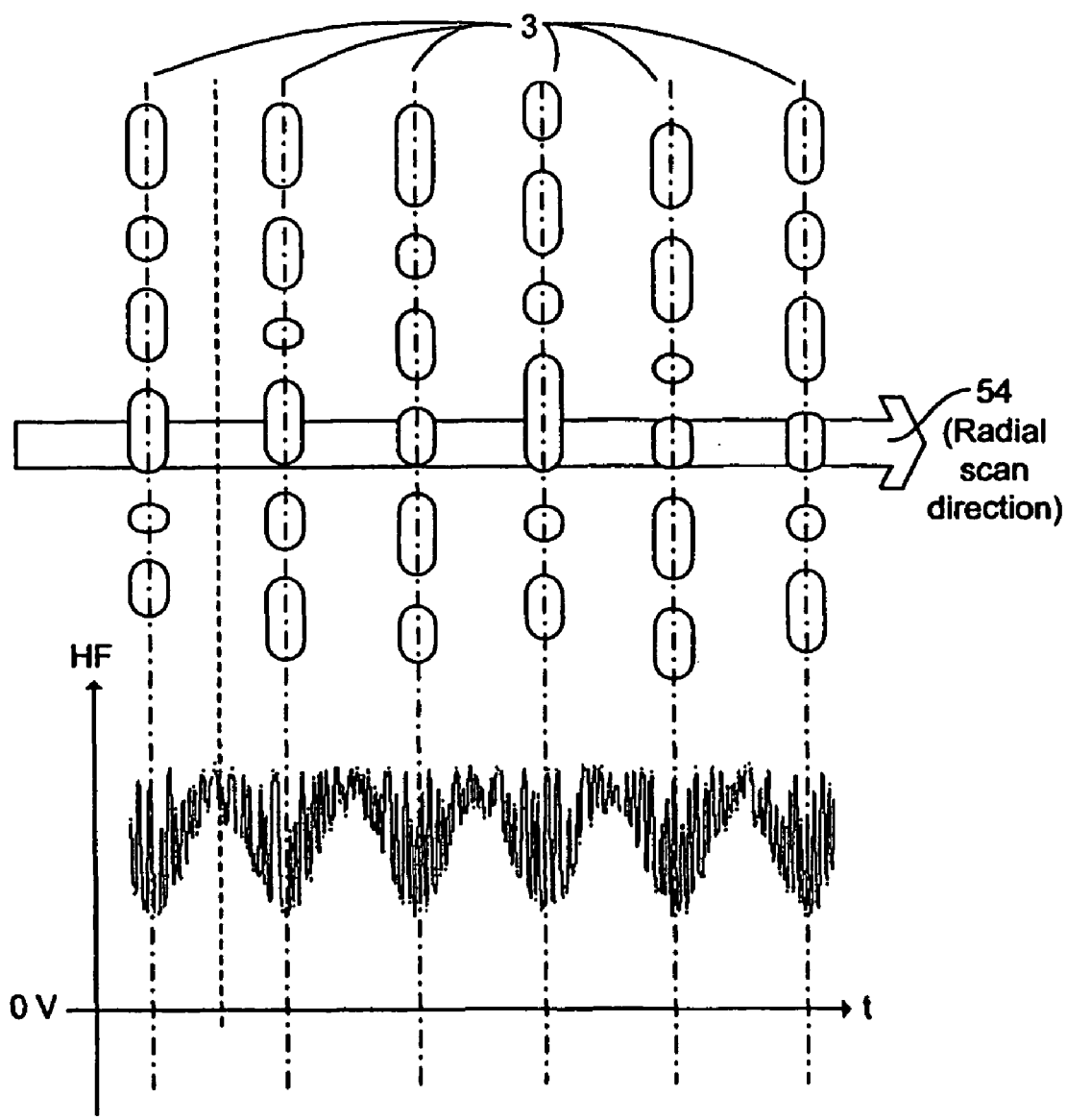
FIG. 5 illustrates a one-beam radial scan detection principle, which may be used in conjunction with a preferred embodiment of the invention.

FIG. 5 is a more detailed view of the underlying principles for producing the composite HF-signal. When the radial scan mechanism of the laser scan unit 20 moves the optical read device 21 in a radial direction 54 across the surface of the optical disk 1, the resulting output signal HF from the laser scan unit 20 will contain the two mainly sinusoidal signal components found in FIG. 4a and FIG. 5. As mentioned above, the low frequency envelope signal will reach a local minimum every time the scanning laser beam passes across the centers of the pits 6 and will reach a local maximum when the laser beam passes the land area between adjacent pits 6. During the passages over the tracks, the envelope signal will AM-modulate the high-frequency signal arising from the passages of the pit and land regions as mentioned above. Due to the fact that the laser spot has a greater diameter than the actual track 3, an irrelevant high-frequency signal will be produced as the spot passes between two adjacent tracks 3, i.e. the high-frequency signal will contain information from both adjacent tracks 3.

In this context it is understood that the track speed, i.e. the speed by which the pits move past the reading device 21 when the disk 1 is revolving, is much greater than the speed of the laser scan unit 20 when it moves in the radial direction of the disk 1 (i.e. the radial scanning speed). By this difference in speed, the reading device 21 will be focused on a track 3 for a sufficient amount of time to detect a sequence of pits and lands. The amount of detected pits will hence vary dependent on the radial scanning speed as well as the track speed. In a preferred embodiment, a sequence of 5 to 20 pits will be sufficient for performing the measurement procedure described below.

In a preferred embodiment, the composite signal is sampled and converted into digital form by an Analog-to-Digital converter (ADC) 30 before further processing. By doing so, the flexibility of the system is increased since the subsequent processing of the composite signal is more easily performed in the digital domain, rather than in the analog counterpart, since new functions and calculation algorithms may be implemented in the digital domain without hardware modifications.

The composite signal is then received in a processing device 40, which comprises a controller 41, a RAM memory 45a, a ROM memory 45b and a hard disk 45c, as is indicated in FIG. 3. The controller 41 is also connected to input devices such as a keyboard 46 and a mouse 47, as well as to an output device such as a display 48. As will be described in more detail in the following, the controller 41 will in a preferred embodiment execute a quality-testing algorithm by executing programs instructions stored in any of the memories 45*a*, 45*b* or 45*c*. The quality-testing algorithm will determine a measure as to the quality of the optical disk 1 with respect to amplitude parameters in response to the time-varying measurement signal (HF) obtained by the laser scan unit 20.

The controller 41 may be implemented by any commercially available microprocessor. Alternatively, another suitable type of electronic logic circuitry, for instance an Application-Specific Integrated Circuit (ASIC) or a Field-Programmable Gate Array (FPGA) may substitute the controller 41. Correspondingly, the memories 45*a*, 45*b*, 45*c*, the input devices 46, 47 and the output device 48 may all be implemented by commercially available components and are not described in any detail herein.

For clarity reasons, the quality-testing algorithm described below is divided into different functional blocks. It should, however, be emphasized that these blocks may be implemented in-hardware as well as in software.

In order to achieve correct measurements, the rotational speed of the optical disk 1 has to be adapted to the radial position of the optical read device 21. This is because as the optical read device 21 moves outward from the center of the disk 1, the pits move past the optical read device at a faster rate (the tangential speed of the pits is equal to the radius times the speed at which the disc is revolving). As an alternative, since the relationship between tangential speed and radial position is known, the processing device 40 may subsequently compensate for effects arisen from readings at different radial positions.

The signal from the ADC 30 is fed into a selecting block 42 where relevant information signal parts are extracted from the composite signal. As the signal envelope will provide information whether the laser spot is at the center of a track 3 or somewhere in-between two tracks 3 (i.e. land) the selecting block 42 is able to define a time window, in which relevant information is residing. FIG. 4*a* illustrates the composite signal where the relevant information related to a single track is residing in a sequence of time slots $t_{R1}$-$t_{Ri}$ defined by the envelope signal. The remaining part of the signal, defined by timeslot $t_{N1}$-$t_{Ni}$, comprises signal information that is a blend of information from two adjacent tracks, i.e. no relevant information is residing in this part of the signal.

Figure 4B:

After processing in the selecting block 42, the signal is in the form shown in FIG. 4*b*. As can be seen from FIG. 4*b*, the time slot $t_N$ may be used for subsequent processing and evaluation of the composite signal residing in timeslot $t_R$. It should be emphasized in this context that the selection of the relevant signal parts may be performed in the digital domain as well as in the analog domain. As an example of the latter, a controllable switch may select the relevant parts of the signal before feeding the signal into the ADC 30.

Figure 4C:
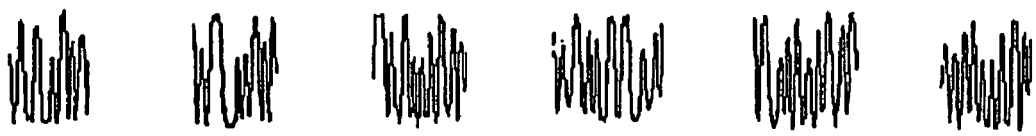

The next block, the measuring block 43, receives the sequence of relevant signal information from the selecting block 42. In order to simplify the measure of the signal levels of the relevant signal portion, an inverse envelope function is applied to the information signal. By this procedure, the signal levels within a timeslot $t_R$ will have the same reference voltage independent of where in the time slot the measurement is performed. FIG. 4*c* shows the relevant signal information after envelope compensation. It is understood in this context that the signals illustrated in FIGS. 4*a*-4*c* according to a preferred embodiment are in the form of binary numbers, since the conversion from the analog domain into the digital domain takes part before the processing of the signals. For clarity reasons, however, the signals are illustrated as analog signals.

After envelope compensation, the processing device 40 measures the signal amplitude by investigating the values of the sampled and compensated information signal at every time instant. The information signal is preferably stored in the RAM memory 45*a* or on the hard disk 45*c*.

An identifying block 44 in the processing device determines if any $I_3$ or $I_{11}$ signal components produced by pits or distances between pits of length 3T, 11T, or 14T (DVD) levels are present in the actual time slot $t_R$. The top value $I_{TOP}$ of is also determined in order to produce the ratio $I_3/I_{TOP}$ and $I_{11}/I_{TOP}$. The signal levels $I_3/I_{top}$ $I_{11}/I_{top}$ are based on information from more than one timeslot.

The symmetry of the $I_3$ and $I_{11}$ signal levels in respect to the midpoint levels of the signals is also determined according to the formula: $(I_{3MID}-I_{11MID})/I_{11}$. Symmetry=0 is obtained if the midpoints of the $I_3$ and $I_{11}$ signals are at the same level. Signal symmetry is essential since decoder problems will arise in case the signal is very asymmetrical.

Figure 6:
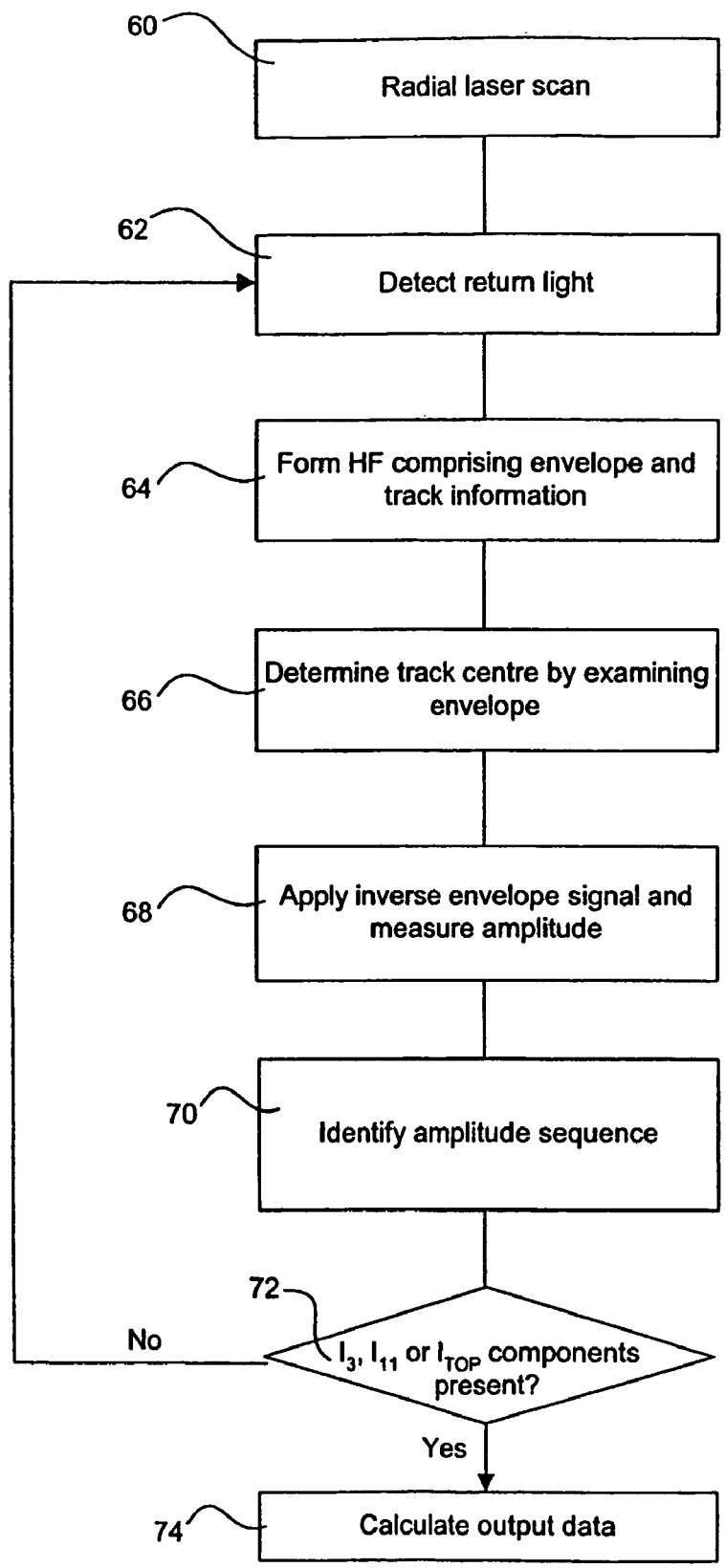
FIG. 6 is a schematic flowchart diagram of a quality-testing method according to the invention.

With reference to FIG. 6, the controller 41 of FIG. 3 is programmed, in the preferred embodiment, to perform a quality-testing algorithm by reading a set of program instructions stored in any of the memories 45*a*, 45*b* or 45*c* and executing the program instructions sequentially. In the flowchart of FIG. 6, the introductory steps 60, 62 and 64 represent the operations carried out by the laser scan unit 20 and analog-to-digital converter 30, as described above.

Next, in step 66, the selecting block 42 will examine the composite signal and determine if the laser spot is focused on a track or in between two adjacent tracks. A low-pass filtering of the composite signal, which will block the information signal and pass through the envelope signal, will result in an extraction of the envelope signal from the composite signal. By examining e.g. the derivative of the envelope signal, the selecting block 42 is able to determine if the envelope signal is at its lowest value, where the relevant high frequency information is found. Since the frequency of the envelope signal is constant, or at least known, the selecting block 42 will be able to apply a window function to the composite signal, which selects a portion of the composite signal surrounding the lowest value.

In step 68, the selected portions of the composite measurement signal are supplied to the measuring block 43, which will examine the sampled and analog-to-digital converted signal in order to determine the amplitude of the signal at every time instant. The processing of the information signal starts by applying an inverse envelope signal to the selected portions of the signal for simplifying the detection of $I_3$, $I_{11}$, and $I_{TOP}$ signal levels.

Then, in a step 70, the measuring block 43 provides the identifying block 44 with information concerning the different amplitude values found in the information signal. As mentioned above, the amplitude values are directly related to the different pit-lengths found in a track 3. The identifying block 44 then identifies the different amplitude values found in the sequence.

In step 72, the identifying block 44 determines if any $I_3$, $I_{11}$ or $I_{TOP}$ component values are present in the sequence. In a preferred embodiment, the identifying block uses information from one or more sequences of pits and lands, i.e. information from more than one track.

If not, the execution is returned to the beginning of step 62. On the other hand, if any of the relevant amplitude values are found in the sequence, a calculating block 49 calculates the $I_3/I_{TOP}$ and $I_{11}/I_{TOP}$ values. The calculating 49 block also examines the $I_3$ and $I_{11}$ values in order to determine if the signals are symmetrical in respect of a common bias level. If the signals do not exhibit symmetry, the controller 40 may generate an alarm or provide another type of output through e.g. the display 48 in step 74.

Alternatively, the controller 40 may simply log all such detected symmetry errors and other output data on the hard disk 42 for later off-line use.

Even if the description above has referred to an optical disk having a single continuous spiral pattern of pits and plane areas, forming in essence a large number of concentric interconnected tracks, it is envisaged that the present invention may also be applied to other optical media, containing not a single spiral pattern but a plurality of non-connected circular or annular information tracks.

It is also envisaged that the quality-testing method of the invention may be embodied as a computer program product, which is stored in a computer-readable form on a suitable record medium (such as an optical or magneto-optical disk, a magnetic hard disk, an electronic memory) and/or is transferred as optical, electric or electromagnetic signals across a computerized network, and which contains a plurality of program instructions that, when read and executed by a computer, will perform the method according to the invention.

The present invention has been described above with reference to a preferred embodiment. However, other embodiments than the one described above are equally possible within the scope of the invention, as defined by the attached patent claims.

The invention claimed is:

1. A signal quality testing apparatus for an optical disk of the type that stores optically readable information in the form of a spiral or annular pattern defining a plurality of concentric tracks, comprising:
    an optical read device;
    a drive mechanism adapted to move the optical read device radially over a portion of the disk surface across at least some of said tracks; and
    a processing device adapted to select portions of a time variant measurement signal received from said optical read device, said measurement signal being associated with passages of the moving optical read device across respective tracks, and wherein the processing device is adapted to measure a signal amplitude in said portions, wherein said signal amplitude being measured in said portions as to identify at least one signal pattern associated with said signal information in said tracks.

2. The signal quality testing apparatus according to claim 1, wherein the processing device receives the measurement signal from an analog to digital converter operatively coupled between the optical card device and the processing device.

3. The signal quality testing apparatus according to claim 1, wherein the processing device further comprises memory means for storing program instructions and/or measurement data.

4. The signal quality testing apparatus according to claim 1, wherein the processing device comprises a controller in the form of a field-programmable gate array.

5. The signal quality testing apparatus according to claim 1, wherein the processing device comprises a controller in the form of an application specific integrated circuit.

6. The signal quality testing apparatus according to claim 1, wherein the processing device comprises a controller in the form of a microprocessor.

7. A method for testing signal quality of an optical disk of the type that stores optically readable information in the form of a spiral or annular pattern defining a plurality of concentric tracks, comprising the steps of:
    scanning an optical read device radially over at least a portion of a surface of the optical disk across at least some of said tracks;
    producing a time variant measurement signal associated with passages of the optical read device across respective tracks;
    selecting at least one portion of the measurement signal comprising information related to a single track;
    measuring a signal amplitude in said portions, and
    identifying from the measured signal amplitude in said portions at least one bit pattern associated with the information in said tracks.

8. The method according to claim 7, wherein said portion of the measurement signal is compensated for effects related to the radial scanning.

9. The method according to claim 8, wherein the compensation comprises the step of applying an inverse envelope signal to the measurement signal.

10. The method according to claim 7, wherein the bit pattern is at least a first $I_3$ bit pattern.

11. The method according to claim 7, wherein the bit pattern is at least a first $I_{11}$ or $I_{14}$ bit pattern.

12. The method according to claim 7, wherein the bit pattern is at least a first $I_{TOP}$ bit pattern.

13. The method according to claim 7, wherein the speed by which the radial scanning is performed is lower than the track speed.

14. The method according to claim 7, further comprising the step of:
    calculating the ration $I_3/I_{TOP}$ and $I_{11}/I_{TOP}$.

15. The method according to claim 7, further comprising the step of:
    determining a level of symmetry of the $I_3$ and $I_{11}$ bit pattern.

16. A computer-readable medium having embodied thereon a computer program for processing by a processor, said processor being operatively coupled to an optical read device and a drive mechanism adapted to move the optical read device radially over a portion of the surface of a disk, said disk being of the type that stores optically readable information in the form of a spiral or annular pattern defining a plurality of concentric tracks, across at least some of said tracks as to produce a time variant measurement signal, said computer program comprising:
    a code segment for selecting at least one portion of the time variant measurement signal when executed by said processor, and
    a code segment for measuring a signal amplitude in the portions when executed by the processor.

17. A computer-readable medium having embodied thereon a computer program for processing by a processor, said processor being operatively coupled to an optical read device and a drive mechanism adapted to move the optical read device radially over a portion of the disk surface across at least some of said tracks as to produce a time variant measurement signal, said computer program comprising:
    a code segment for selecting at least one portion of the time variant measurement signal when executed by said processor, and
    a code segment for measuring a signal amplitude in said portions.

* * * * *